(12) United States Patent
Eckerbom et al.

(10) Patent No.: US 6,896,713 B1
(45) Date of Patent: May 24, 2005

(54) LIQUID SEPARATOR WITH HOLDER UNIT

(75) Inventors: Anders Eckerbom, Vaxholm (SE); Per Lindestam, Järfälla (SE)

(73) Assignee: Artema Medical AB, Sundbyberg (SE)

( * ) Notice: Subject to any disclaimer, the term of this patent is extended or adjusted under 35 U.S.C. 154(b) by 0 days.

(21) Appl. No.: 09/890,583

(22) PCT Filed: Jan. 20, 2000

(86) PCT No.: PCT/SE00/00113

§ 371 (c)(1),
(2), (4) Date: Nov. 2, 2001

(87) PCT Pub. No.: WO00/45884

PCT Pub. Date: Aug. 10, 2000

(30) Foreign Application Priority Data

Feb. 2, 1999 (SE) .................................. 9900351

(51) Int. Cl.$^7$ ................... A61M 16/08; A61B 05/08

(52) U.S. Cl. ..................... 55/421; 55/510; 73/23.3; 422/84; 600/532; 600/543; 96/187; 96/189; 96/417

(58) Field of Search ............... 210/435–436, 210/150–151, 218, DIG. 6, 532.1, 538–539, 210/180, 188, 85, 91, 154, 234, 239, 240, 210/232, 103, 235, 97; 55/355, 421, 394, 55/495, 510, 490, 514, 410, 417, 466, DIG. 17; 96/417, 423, 187–189, 192; 604/405–406, 604/407; 422/84; 73/23.3; 600/532, 543; 128/205.12

(56) References Cited

U.S. PATENT DOCUMENTS

| | | | | |
|---|---|---|---|---|
| 3,066,462 A | * | 12/1962 | Yap et al. ...................... | 95/287 |
| 3,261,145 A | * | 7/1966 | Paulson et al. ............... | 95/111 |
| 3,572,008 A | * | 3/1971 | Hankison et al. ............. | 95/105 |
| 4,298,358 A | * | 11/1981 | Ruschke ....................... | 96/174 |
| 4,592,368 A | * | 6/1986 | Ricciardelli et al. ........ | 600/532 |
| 4,717,403 A | * | 1/1988 | Choksi ........................ | 55/429 |
| 5,135,645 A | * | 8/1992 | Sklenak et al. .............. | 210/97 |
| 5,651,887 A | * | 7/1997 | Posner et al. ............... | 210/232 |
| 5,674,381 A | * | 10/1997 | Den Dekker ................ | 210/85 |
| 5,935,281 A | * | 8/1999 | Rotheiser et al. .......... | 55/385.3 |
| 6,051,144 A | * | 4/2000 | Clack et al. ................ | 210/739 |
| 6,120,685 A | * | 9/2000 | Carlson et al. ............. | 210/232 |
| 6,303,031 B1 | * | 10/2001 | Senner ....................... | 210/232 |
| 6,533,926 B2 | * | 3/2003 | Hawkins et al. ............. | 210/85 |
| 6,537,444 B2 | * | 3/2003 | Wilberscheid et al. ........ | 210/85 |
| 6,645,277 B1 | * | 11/2003 | Franz et al. .................. | 96/417 |
| 2002/0144937 A1 | * | 10/2002 | Wilberscheid et al. ........ | 210/85 |

FOREIGN PATENT DOCUMENTS

| | | |
|---|---|---|
| EP | 0 242 790 | 10/1987 |
| EP | 0 549 266 | 6/1993 |

* cited by examiner

Primary Examiner—Terry K. Cecil
(74) Attorney, Agent, or Firm—Young & Thompson

(57) ABSTRACT

A liquid separator for separating liquid from gases, comprises a water trap (1) that includes a container (3), a connector (5) for incoming gas flow, a separation chamber (4) that includes a filter and at least one connection passageway for leading separated gas to an analysis instrument. The water trap (1) can be removably fitted in a holder unit (2) connected to the analysis instrument, and the holder unit (2) includes connection devices (15, 16) for receiving the connection passageway.

13 Claims, 3 Drawing Sheets

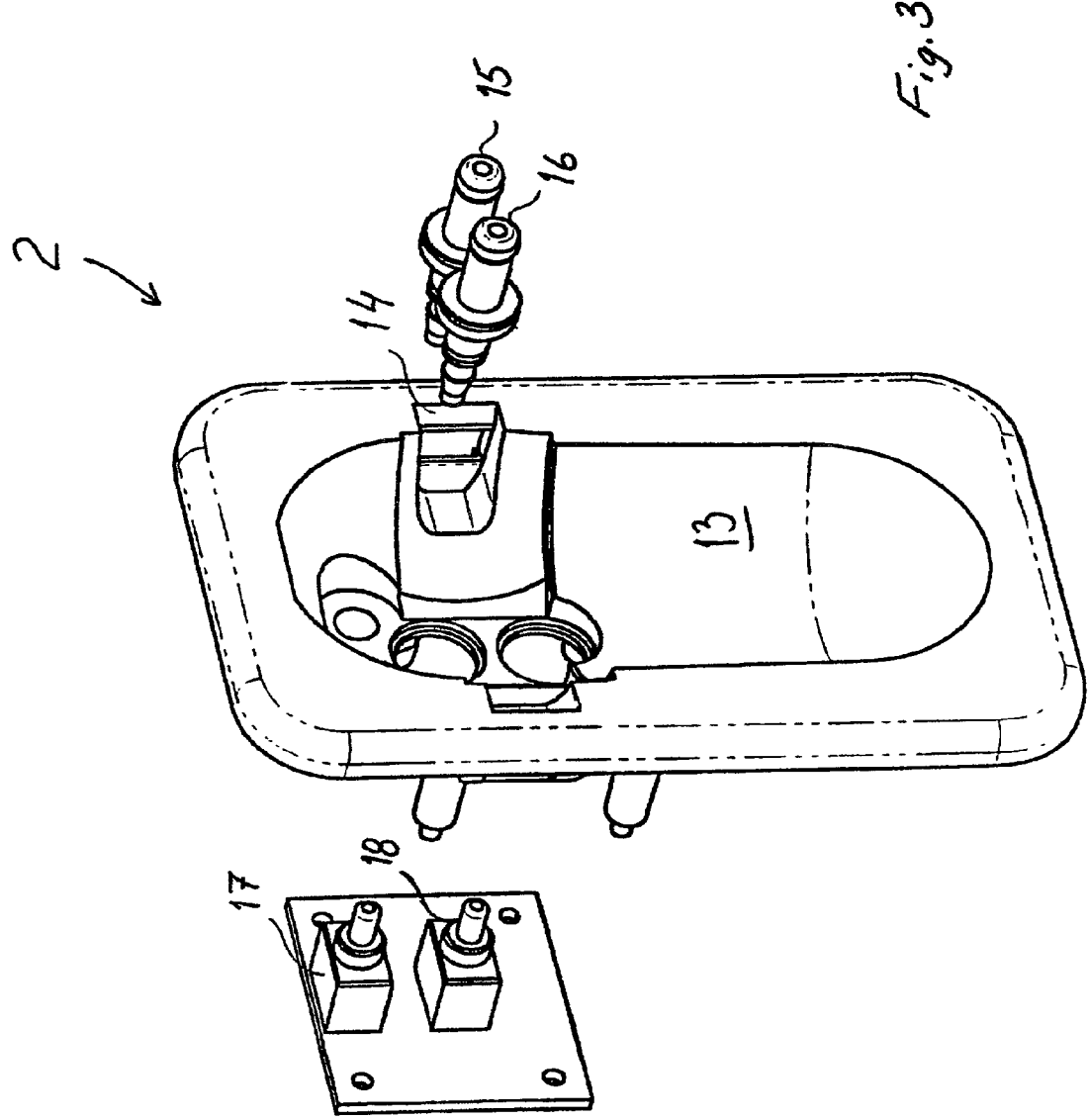

LIQUID SEPARATOR WITH HOLDER UNIT

BACKGROUND OF THE INVENTION

The present invention relates to a liquid separator for separating liquid from gases, and particularly for separating liquids from expiration gases in medical analysis instruments. The invention includes a liquid separator having a water trap and a holder/connection device. The water trap may be a one time use only trap, and the connection device may be a quick-fastener device.

DESCRIPTION OF THE RELATED ART

When a gas sample from expiration gases is led in a patient circuit to an analysis instrument, it is unavoidable that moisture, secretion, blood, bacteria, etc., are liable to accompany the sample. As the temperature falls when the gas sample is led from the patient circuit to the analysis instrument, moisture present in the gas precipitates in the form of water droplets. Should water, blood or secretion enter the analysis instrument, there is a serious risk that the instrument will be permanently damaged, and consequently various protective solutions for preventing such contamination have been proposed in the art.

The simplest method of avoiding the ingress of bacteria, blood and secretion into the gas sample is to place a hydrophobic bacteria filter in the orifice of the sampling conduit proximal to the patient circuit. One drawback with this solution resides in the difficulty of obtaining a filter surface, which is sufficiently large to prevent the rise time of the gas measuring process from being impaired. A filter that has a small surface area will quickly become blocked and there-with result in an interruption in the gas monitoring process.

The presence of a bacteria filter in the orifice of the sampling conduit will not solve the moisture problem, because the moisture does not precipitate from the sample until the sample is downstream of the filter. One solution to this problem is to use a special hose material, Nafion®, which allows moisture to wander freely through the hose wall. This material, however, is very expensive which makes it difficult to obtain viable products when using said material.

Alternatively, water droplets, and possibly also secretion, can be separated from expiration gas in a water trap. A positive, inexpensive and effective separator can be obtained, by combining the water trap with a bacteria filter. However, one drawback with this solution is that the rise time of the gas measuring process will be seriously impaired unless the water trap is adapted with respect to the volume of gas that shall be processed at that particular time.

The need for a short rise time is particularly accentuated when measuring the expiration gas of newly born infants, e.g. neonatal patients. Small children usually have a considerably higher respiration rate than adults. 40–60 breaths per minute is normal for such infants, as compared to about 12 breaths per minute for adults. Thus, in this case the gas sampling system must have a pneumatic rise time of well above 0.5 s in order to carry out a correct gas analysis with respect to time, a rise time of 200 ms being an appropriate value in this respect.

The pneumatic rise time of the gas sampling system is essentially inversely proportional to the sampling flow, in other words a high rate of flow results in a short rise time. Respiration volumes of several liters are normal in the case of adult patients, which enables sample flow rates in the order of 200–300 ml/min to be used without influencing the respiratory circuit. However, in the case of neonatal patients, which have respiratory volumes in the order of decilitres, it is necessary to lower the rate of flow to a minimum. 50 ml/min is a normal flow rate in this latter case. Consequently, when the need for a short rise time is greatest, the possibilities of achieving such a rise time are the worst.

In addition to needing to extract moisture, bacteria, etc., from the expiration gas of a patient, it is also necessary to protect the analysis instrument from dirt and other contaminants present in the ambient air. Many gas analysis instruments have long warm-up times, meaning that the instrument is normally never switched off. Consequently, if the instrument is left switched on for a long period of time in the absence of a protective filter, the measuring chamber of the analyser will gradually become dirty with progressively poorer performances as a result.

Water traps have been the solution that has been used to increasing extents to eliminate moisture in gas samples. EP-A 2-0 549 266 teaches a method of extracting both moisture and other foreign particles with the aid of a hydrophobic bacteria filter. In the case of the water trap described in this prior publication, the gas sample is passed through a passageway that is divided in an upper half and a lower half of the hydrophobic filter. The moist gas sample is led into the front edge of the lower half of a passageway and is caused to exit by applying a strong sub-pressure to an opening in the rear edge of the upper half of said passageway. The liquid extracted by this arrangement is led away by applying a weak sub-pressure to an opening in the rear edge of the lower half of the passageway.

One drawback with this known water trap is that it requires a relatively large filter area, about 1 $cm^2$, in order to ensure that the product will have a sufficient length of life. The length of the passageway is limited chiefly by the desire to obtain the smallest possible unit. A length of about 3.5 cm has been found suitable. Consequently, a passageway diameter of about 3 mm is needed in order to obtain an effective filter surface. Hoses used for gas sampling purposes, however, will normally have an inner diameter of about 1.4–1.5 mm, meaning that eddy currents are generated and impaired rise time obtained when the gas sample reaches the larger diameter of the passageway.

SUMMARY OF THE INVENTION

Accordingly, the object of the present invention is to provide a liquid separator that avoids the aforesaid drawback with the earlier known water trap.

This object is achieved with an inventive liquid separator that has the characteristic features set forth below.

There is provided in accordance with the invention a liquid separator for extracting liquid from gases, said separator comprising a water trap that includes a container, a connection for incoming gas flows, a separation chamber that includes a filter, and at least one connection passageway for conducting separated gas to an analysis instrument, wherein the water trap can be attached removably to a holder unit connected to the analysis instrument, and wherein the holder unit includes connection means for connection of the connecting passageway.

The invention also enables water traps of different sizes to be used for adults and for children, with automatic switching of the analysis instrument in accordance with the size of water trap used.

BRIEF DESCRIPTION OF THE DRAWINGS

The invention will now be described with reference to a non-limiting exemplifying embodiment thereof and also with reference to the accompanying drawings, in which

FIG. 3 is a perspective exploded view of the holder unit shown in FIG. 1.

DESCRIPTION OF THE PREFERRED EMBODIMENTS

Figure 1:
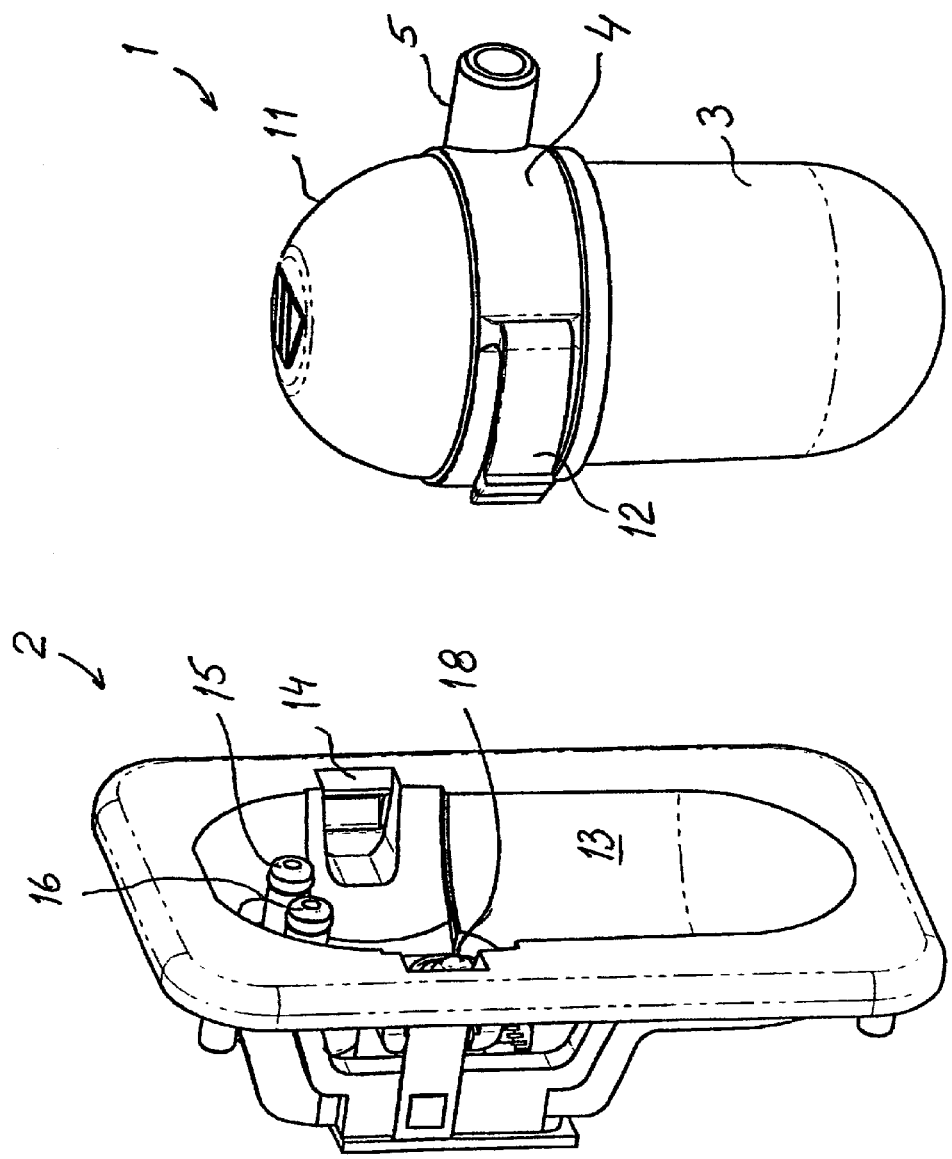
FIG. 1 is a perspective view of an inventive liquid separator, showing the water trap and the holder unit separated from one another.
Figure 2:
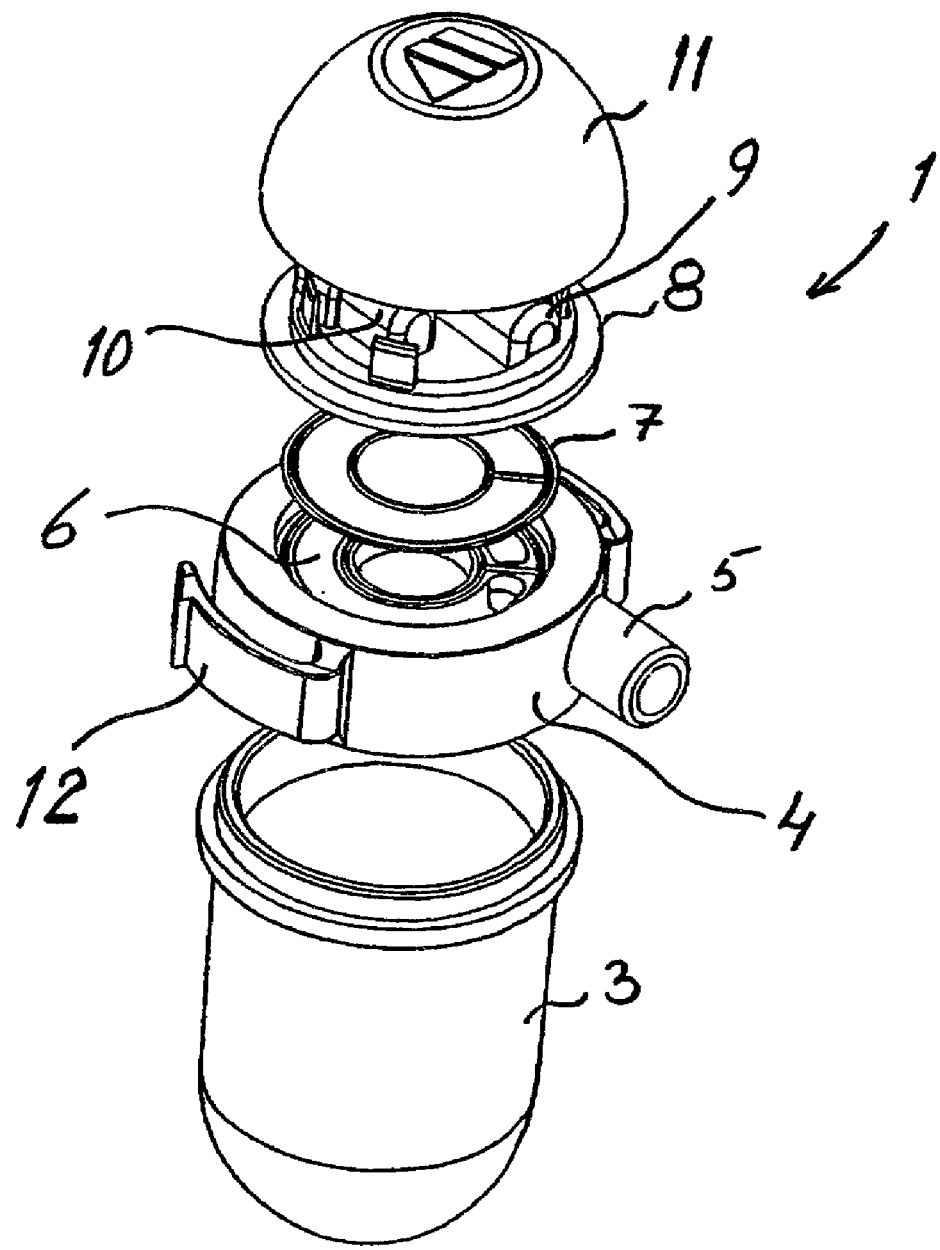
FIG. 2 is a perspective exploded view of the water trap shown in FIG. 1.

The inventive liquid separator comprises two main parts in the form of a water trap 1 and a holder unit 2. The holder unit 2 is a part that can normally be firmly fitted to the instrument (not shown) used to analyse expiration gas. The water trap 1 is a disposable product that is preferably found in two different sizes or two different designs, one for adult patients and one for neonatal patients.

The water trap 1 includes a container 3 located beneath a separation chamber 4 provided with a connection 5 for receiving a gas flow incoming from the patient. The separation chamber includes a liquid passageway 6 and a filter 7 positioned above said passageway, for instance a bacteria filter. Located above the separation chamber 4 and connecting to the other side of the filter 7 is an upper chamber part 8 that includes a gas passageway (not shown) corresponding to the liquid passageway 6 in the separation chamber and leading to connection passageways 9, 10 by which the water trap can be connected to the holder unit 2 and to the analysis instrument respectively. The upper chamber part 8 is covered by a hood or cap 11. The separation chamber 4 is fitted externally with locking tabs 12 which enable the water trap 1 to be snapped firmly to the holder unit 2.

The separation chamber 4 is preferably fixed permanently to the upper chamber part 8, for instance ultrasound welded thereto. The filter 7, which is inserted between the separation chamber and the upper chamber part 8, may be of the PTFE kind and has a pore size of about 0.5 $\mu$m and may be sealed with the aid of a labyrinth seal formed in the separation chamber and the upper chamber part. The container 3 of the water trap is adapted so as to be removable from the separation chamber 4 and therewith enable liquid collected in the container to be emptied therefrom.

The holder unit 2 includes a cavity 13 in which part of the water trap 1 can be accommodated. The holder unit includes locking apertures 14 which receive the locking tabs 12 on the water trap and therewith lock the trap 1 firmly in the holder unit. Two connection devices 15, 16 are provided behind the cavity 13 for receiving the connection passageways of the water trap 1. These connection devices 15, 16 are connected to hoses passing to the analysis instrument. Two electric contact elements 17, 18 are provided in the rear edge of the cavity 13 and are activated by insertion of a water trap 1 into the cavity 13 of the holder unit 2.

The electric contact elements 17, 18 are adapted so that one contact element will detect the presence of a water trap in the holder unit, wherewith when the water trap 1 is removed from the holder unit 2 the contact element will function to immediately stop the flow to the analysis instrument, or will stop said flow after a certain time delay, so that no air and possible contaminants will be sucked into the instrument and contaminate the same. The other electric contact element is adapted to detect the type of water trap inserted into the holder unit. The two different types of water trap mentioned above may be designed differently at the contact region with said other electric contact element, for instance such that when using a water trap intended for children the contact will be pressed in, while providing a water trap intended for adult patients with an aperture which will mean that said other electric contact will not be pressed in when fitting said trap. The second electric contact element will then be arranged so that when it is pressed-in by fitting a water trap intended for neonatal patients, the analysis instrument will be switched to a mode in which it operates with a lower rate of flow.

The two connection passageways 9, 10 are connected to the connection devices 15, 16 of the holder unit 2 so that both a main flow that passes from the water trap to the analysis instrument and a secondary flow that passes through the container of the water trap can be obtained.

The main difference between the two water trap embodiments is that one is intended for adult patients and has a passageway width of about 3 mm, whereas the neonatal model has a passageway width of about 1.4 mm. The smaller passageway width in the neonatal model means that the rise time will be much quicker than in the case of the adult model. In this case, the problems normally occurring with shorter product life lengths are compensated for by using a lower rate of sample flow.

Because the type of water trap used can be identified, the analysis instrument can be set automatically to choose an optimal rate of sample flow for respective models through the medium of said electric contact elements. In the case of the adult model, there is normally used a flow rate in the order of 200–300 ml/min, whereas a flow rate of about 50 ml/min is normally used in the case of the neonatal model. Switching between these flow rates can thus take place fully automatically, without the risk of a wrong setting being made manually.

What is claimed is:

1. A liquid separator for separating liquid from gases, comprising:

the combination of a water trap (1) and a holder unit (2), the water trap (1) including a container (3), a connection (5) for incoming gas flow, a separation chamber (4) that includes a filter (7), and at least one connection passageway (9, 10) for leading liquid-free gas to an analysis instrument via the holder unit, the holder unit being connectable to the analysis instrument, the water trap (1) removably fitted in an external cavity of the holder unit (2), the holder unit (2) provided with at least one connection device (15, 16) for accommodating the connection passageway (9, 10) within the external cavity, and the holder unit (2) including a first electric contact element (18) which functions to detect the presence of a water trap (1) in the holder unit and to stop the flow of sample gas to the analysis instrument when no water trap is fitted in the holder unit, characterised in that the holder unit (2) includes a second electric contact element (17) which functions to detect the type of water trap (1) fitted in the holder unit and to adjust a flow rate of the analysis instrument in accordance with the type of water trap used.

2. A liquid separator according to claim 1, characterised in that the connection device (15, 16) is a quick-fastener device for connection to the connection passageway (9, 10).

3. A liquid separator according to claim 1, characterised in that the water trap (1) includes two connection passageways (9, 10), and in that the holder unit (2) includes two connection devices (15, 16).

4. A liquid separator according to claim 1, characterised in that the water trap (1) is designed in different sizes for infants and adults; and in that one size of the water trap includes a contact region to actuate the second electric contact element (17) of the holder unit.

5. A liquid separator, comprising:
a holder unit (2); and
a water trap (1) externally held by the holder unit,
the holder unit with connections to an instrument used to analyze expiration gas,
the holder unit configured to externally hold water traps of two different types,
the water trap comprising
a separation chamber (4) provided with a connection (5) to receive a gas flow incoming from a patient,
a container (3) located beneath the separation chamber,
a liquid passageway (6) within the separation chamber and a filter (7) positioned above the passageway,
an upper chamber part (8) located above the separation chamber (4) and connecting to an upper side of the filter,
two connection passageways (9, 10), within the upper chamber part, connected via the filter to the separation chamber, the two connection passageways being connectable to the holder, and via the holder to the instrument,
locking tabs fitted externally to the separation chamber and engageble with corresponding elements of the holder to externally snap-fit the water trap to the holder unit and allow a user to remove the water trap from the holder,
the holder comprising two connection devices (15, 16),
the two connection passageways (9, 10) are connectable to the two connection device, and
the two connection devices having outlets connectable to the instrument,
the two connection passageways, when connected to the connection devices of the holder unit, providing a main flow from the water trap to the instrument through a first of the two passageways and a secondary flow from the water trap to the instrument through a second of the two passageways,
the holder further comprising two electric contact elements (17, 18) provided in a rear edge of the cavity and activated by insertion of a water trap into the cavity,
a first of the contact elements configured to detect the presence of a water trap in the holder unit, so that when the water trap is removed from the holder unit, the contact element will function to stop a flow to the instrument, and
a second of the contact elements is configured to detect the type of water trap inserted into the holder unit.

6. The separator of claim 5, wherein the separation chamber is welded to the upper chamber part 8, and the filter is a bacteria filter.

7. The separator of claim 5, wherein the filter is a PTFE bacteria filter sealed with a labyrinth seal formed in the separation chamber and the upper chamber part.

8. The separator of claim 5, wherein,
the filter is a bacteria filter,
the container is removable from the separation chamber to enable liquid collected in the container to be emptied therefrom.

9. The separator of claim 5, wherein the holder unit comprises an external receiving cavity (13) which holds the water trap.

10. The separator of claim 9, wherein the corresponding elements of the holder, to which the locking tabs are engageble with to externally snap-fit the water trap to the holder unit, are locking apertures (14) which receive the locking tabs on the water trap and therewith lock the trap in the holder unit.

11. The separator of claim 5, wherein,
a first type of water trap presses in the second of the contact elements and the second of the contact elements signals the instrument to operate at a lower rate of flow than a maximum rate of flow, and
a second type of water trap which does not press against the second of the contact elements.

12. A liquid separator, comprising:
a holder unit (2) with an external cavity and connectable with expiration gas analysis instrument; and
a water trap (1) externally held by the holder unit within the cavity,
the water trap comprising
a separation chamber (4) provided with a connection (5) to receive a gas flow incoming from a patient,
a container (3) located beneath the separation chamber,
a liquid passageway (6) within the separation chamber and a filter (7) positioned above the passageway,
an upper chamber part (8) located above the separation chamber (4) and connecting to an upper side of the filter,
two connection passageways (9, 10), within the upper chamber part, connected via the filter to the separation chamber, the two connection passageways being connectable to the holder, and via the holder to the instrument, one of the passageways providing liquid-free gas to the analysis instrument,
locking tabs fitted externally to the water trap and engageble with corresponding elements of the holder to externally and removably fit the water trap to the holder unit to allow a user to remove the water trap from the holder, wherein,
the holder comprises two connection devices (15, 16), and
the two connection passageways are connectable to the two connection devices,
the two connection devices having outlets connectable to the instrument,
the holder unit is configured to externally hold water traps of two different types,
the holder further comprises two electric contact elements (17, 18) activated by insertion of the water trap of each type into the cavity,
a first of the contact elements configured to detect the presence of a water trap in the holder unit, so that when the water trap is removed from the holder unit, the first contact element will function to stop a flow to the instrument, and
a second of the contact elements configured to detect the type of water trap inserted into the holder unit and control a flow rate of the instrument based on the detected type of water trap.

13. The separator of claim 12, wherein,
the filter is a bacteria filter, and
the container is removable from the separation chamber to enable liquid collected in the container to be emptied therefrom.

* * * * *